United States Patent [19]

Colone

[11] Patent Number: 4,822,341

[45] Date of Patent: Apr. 18, 1989

[54] VASCULAR ACCESS FISTULA

[75] Inventor: William M. Colone, Phoenix, Ariz.

[73] Assignee: Impra, Inc., Tempe, Ariz.

[21] Appl. No.: 123,339

[22] Filed: Nov. 20, 1987

[51] Int. Cl.⁴ .............................................. A61M 5/00
[52] U.S. Cl. ....................................... 604/175; 604/4;
604/249
[58] Field of Search ...................... 604/175, 52, 4, 8, 9,
604/249, 256, 280, 33

[56] References Cited

U.S. PATENT DOCUMENTS

| | | | |
|---|---|---|---|
| 3,765,032 | 10/1973 | Palma | 3/1 |
| 3,826,257 | 7/1974 | Buselmeier | 604/8 |
| 4,015,601 | 4/1977 | Bokros et al. | |
| 4,092,983 | 6/1978 | Slivenko | |
| 4,108,173 | 8/1978 | Slivenko et al. | |
| 4,164,221 | 8/1979 | Bentley et al. | |
| 4,187,390 | 2/1980 | Gore | 174/102 |
| 4,350,157 | 9/1982 | Hoffa | |
| 4,405,319 | 9/1983 | Consentino | 604/175 |
| 4,496,349 | 1/1985 | Cosentino | 604/175 |
| 4,512,761 | 4/1985 | Raible | 604/8 |
| 4,578,063 | 3/1986 | Inman et al. | 604/175 |
| 4,596,350 | 1/1985 | Cosentino | 604/175 |
| 4,639,247 | 1/1987 | Bokros | 604/175 |
| 4,648,391 | 3/1987 | Ellis | 604/175 |
| 4,654,033 | 3/1987 | Lapeyre et al. | 604/175 |

OTHER PUBLICATIONS

"Hemasite Vascular Access System-The Original Button Shunt", advertisement published by Renal Systems, Inc., of Minneapolis, Minn.
"Proven Vascular Access-The Bentley DiaTAP Button", advertisement published by American Bentley.
Bennion and Wilson, "Hemodialysis and Vascular Access", *Vascular Surgery*, Chapter 22, pp. 625-662, 1983.

*Primary Examiner*—Stephen C. Pellegrino
*Attorney, Agent, or Firm*—Cahill, Sutton & Thomas

[57] ABSTRACT

A vascular access fistula includes a smooth, continuous PTFE tube having a hard sintered tube section integrally joined at its opposing ends with expanded PTFE tube sections. Inlet and outlet access port holes are formed in the hard sintered tube section to provide acute access to the fistula. A port collar surrounds the hard sintered tube section to facilitate the attachment of dual lumen tubing thereto. Following implantation of the access fistula, the dual lumen tubing temporarily extends through the skin to provide acute access while the access fistula heals. The port collar houses a slide valve which selectively couples the inlet and outlet access port holes to the dual lumen tubing for acute access. After the access fistula has healed, the slide valve is closed, the dual lumen tubing is cut off from the port collar, and chronic vascular access is provided by percutaneous cannulation of the implanted PTFE tube.

22 Claims, 2 Drawing Sheets

VASCULAR ACCESS FISTULA

BACKGROUND OF THE INVENTION

1. Field of the Invention

The present invention relates generally to implantable blood access devices of the type used to perform hemodialysis, and more specifically, to an implantable vascular access fistula providing both acute external access, as well as chronic access via percutaneous cannulation.

2. Description of the Prior Art

Hemodialysis is now a commonly practiced method of treating patients suffering from renal failure. Hemodialysis machines serve to remove life-threatening chemicals from the blood stream, when the kidneys themselves can no longer effectively remove such chemicals. In order to perform hemodialysis, access must first be obtained to the blood flow system.

Various blood access devices have been developed to facilitate direct access to the vascular system. The Scribner arteriovenous shunt described by Quinton et al., "Cannulation of Blood Vessels For Prolonged Hemodialysis", Trans Am Soc Artif Organs 6: 104–113, 1960, includes a length of Silastic tubing having catheter tips at each end. The catheter tips are inserted into an artery and a vein below the skin, while the Silastic tubing extends primarily external to the skin, except at the ends thereof where it passes through the skin. Such external shunts are plagued by infection at the entrance sites where the Silastic tubing passes through the skin, as well as by clotting problems. External shunts further pose an inconvenience to the patient because of the extra care which needs to be taken to avoid injury or dislodgment of the Silastic tubing.

Many of the problems arising from the external Scribner shunt are avoided by the formation of a subcutaneous autogenous arteriovenous fistula, such as the type known as the Brescia-Cimino fistula, which is formed using the cephalic vein and the radial artery in the forearm. Arterial pressure causes contiguous veins to dilate and provide sites for venipuncture. However, such a fistula may not be punctured for several weeks because of the time required for the walls of the dilated vein to thicken.

Several atraumatic vascular access devices are known wherein repeated percutaneous needle punctures may be avoided. One such device is known as a Buselmeier shunt and is described in U.S. Pat. No. 3,826,257 issued to Buselmeier. The Buselmeier shunt, like the Scribner shunt, provides a length of Silastic tubing having vessel tips at each end to be cannulated into an artery and an adjacent vein. In the Buselmeier shunt device, the shunt tube is U-shaped and is intended to be implanted below the skin. Extending from the Silastic shunt tube are one or two access tubes which project outwardly through the skin where a closure plug is installed to seal off the access tubes. The closure plugs are removed when dialysis is to be perfomed.

Button shunt devices are also known wherein a skin level port is provided to avoid the need for percutaneous needle puncture One such button shunt device is commercially available under the registered trademark "HEMASITE" from Renal Systems of Minneapolis, Minn. This device is described in U.S. Pat. No. 4,496,350 issued to Cosentino and assigned to Renal Systems. The "HEMASITE" device includes a T-shaped body having lengths of expanded polytetrafluoroethylene (PTFE) tubing secured to opposing ends thereof for the purpose of interconnecting the device between an artery and a vein. Extending upwardly from the T-shaped body is a stem which protrudes permanently through the skin. The stem includes a septum which normally precludes blood flow outwardly therethrough. The external end of the stem is normally closed by a removable cap. When access is desired, the cap is removed and a dual-needle assembly that mates with the stem is inserted therein to pass through the septum for communicating with the bloodstream.

Another button-type shunt is commercially available under the trademark "DiaTAP" from American Bentley, a subsidiary of American Hospital Supply Corporation of Irvine, Calif. This device is described in U.S. Pat. No. 4,164,221 issued to Bentley et al. and assigned to Bentley Laboratories. The device includes a stem which extends upwardly from a length of expanded PTFE tubing, passing just above the skin at its upper end to provide a permanent skin level port. A plug normally fits within the stem to prevent blood from flowing outwardly therethrough. A removable cap retains the plug within the stem until access is desired. A special valved connector is coupled to the external end of the stem for controlling blood flow therethrough when access is desired.

While the aforementioned atraumatic vascular access devices avoid percutaneous needle puncture, such devices still present the risk of infection inherent in any device which permanently passes through the skin. Moreover, discontinuities within the blood flow path provided by such prosthetic devices often cause a buildup of clotted blood which may restrict or ultimately seal off the flow of blood therethrough, resulting in thrombosis. Such discontinuities arise, for example, in the "HEMASITE" device wherein the T-shaped body is joined with the surrounding PTFE tubing, and in the "DiaTAP" device at the point where the stem is secured to the expanded PTFE tubing.

Apart from the atraumatic vascular access devices discussed above, prosthetic vascular grafts, or bridge fistulas, are also known wherein the graft is implanted entirely below the skin to provide a readily palpable conduit that can easily be cannulated by a needle to obtain access for hemodialysis. Such prosthetic vascular grafts are often connected within the vascular system between the distal radial artery and the cephalic or basilic vein. Each end of the fistula is anastomosed in an end-to-side fashion to the respective artery or vein. The most commonly used material to form prosthetic vascular grafts is expanded polytetrafluoroethylene (PTFE) U.S. Pat. No. 4,187,390 issued to Gore discloses a process which may be used to produce highly porous, expanded PTFE structures. PTFE vascular grafts are commercially available under the registered trademark "IMPRA" from IMPRA, Inc. of Tempe, Ariz. Methods of implanting such prosthetic vascular grafts are described in Bennion et al., "Hemodialysis and Vascular Access", Vascular Surgery, pp. 625–662, 1983.

When a physician decides to implant a PTFE vascular graft to provide vascular access following renal failure, the physician must also decide whether or not to simultaneously place a subclavian or jugular vein catheter within the patient to provide temporary acute access to the blood system until the PTFE vascular graft is well-healed. PTFE grafts are highly porous, and surrounding body tissues ultimately grow into the walls of the PTFE vascular graft, resulting in a more natural blood vessel. However, the healing process, during which tissue ingrowth occurs, takes approximately two weeks in most patients. Cannulation of the PTFE vascular graft prior to healing often results in hematoma formation, false aneurysm, leaking of blood from the puncture site, and early fistula failure.

The risks of premature cannulation of the graft can be avoided by short-term placement of a catheter to gain temporary vascular access while the graft heals. However, placement of a subclavian or jugular vein catheter within the patient also presents certain risks. Obviously, the need to perform two surgical operations simultaneously instead of only one complicates surgery. Moreover, placement of a subclavian or jugular vein catheter may result in hemothorax, pneumothorax and other complications. Recently, subclavian vein thrombosis has become a major concern because its presence limits the number of potential fistula sites.

It is an object of the present invention to provide an implantable blood access device for use in performing hemodialysis which avoids the use of tubes or other skin level ports that permanently pass through the skin, in order to minimize long-term infection risks.

It is another object of the present invention to provide an implantable access fistula that permits acute external access to the vascular system for permitting the fistula to become well-healed, while further permitting chronic access to the vascular system by percutaneous cannulation of the fistula.

It is yet another object of the present invention to provide such an implantable fistula which includes a smooth, continuous flow surface to minimize the risk of thrombosis.

Still another object of the present invention is to provide a PTFE vascular graft wherein acute access may be obtained without prematurely puncturing the walls of the graft, and without the need to place a subclavian or jugular catheter within the patient.

A further object of the present invention is to provide a PTFE tube structure which is adapted to be cannulated subcutaneously in the manner of conventional PTFE vascular grafts, while simultaneously including a hardened portion through which acute access may be obtained without disturbing the healing of the PTFE tube and without creating any discontinuities therein.

These and other objects of the present invention will become more apparent to those skilled in the art as the description thereof proceeds.

SUMMARY OF THE INVENTION

Briefly described, and in accordance with one embodiment thereof, the present invention relates to an access device for implantation within a fluid path, such as a vascular system, of a living body, the access device including an implantable graft having a relatively rigid tube section surrounded by and continuous with first and second opposing pliable tube sections. At least one access port hole is formed in the tubular wall of the rigid tube section to facilitate access to the interior of the implantable graft. A valve structure is disposed proximate to the access port hole. A flexible access tube has a first end communicating with the valve structure and a second end opposite therefrom. The valve structure has an opened position for selectively establishing fluid communication between the flexible access tube and the access port hole, as well as a closed position for sealing the flexible access tube from the access port hole.

The implantable graft is adapted to lie entirely below the skin immediately following implantation, except for the flexible access tube, which passes through the skin temporarily until the implantable graft heals. While the graft heals, access to the internal fluid system can be obtained via the second end of the flexible access tube, external to the living body. After the graft has healed, the valve is closed, the flexible access tube is cut from the valve structure, and the implantable graft then lies completely below the skin. Access to the internal fluid system of the living body may thereafter be obtained via percutaneous cannulation of the implantable graft.

The implantable graft may advantageously serve as an access fistula for the vascular system. The relatively rigid tube section, and surrounding pliable tube sections, are preferably formed of a single, continuous length of PTFE tubing having a hard sintered unexpanded PTFE tube section continuous with opposing, expanded PTFE tube sections to provide a smooth, continuous blood flow path. The access porthole is formed in the tubular wall of the hard sintered unexpanded tube section. A port collar formed of an implantable plastic is secured over and around the hard sintered unexpanded PTFE tube section and houses the valve structure. The port collar has a hole formed therein overlying and in fluid communication with the access port hole, and the first end of the flexible access tube is coupled to the port collar in fluid communication with the hole formed therein.

The valve structure may advantageously be provided by a slide member which slides within a channel formed in the port collar. In its opened position, the slide member selectively establishes a continuous path between the access port hole and the first end of the flexible access tube. When the slide member is moved to its closed position, it seals the hole formed in the port collar and interrupts fluid communication between the access port hole and the first end of the flexible access tube.

Preferably, a second access porthole is also formed in the hard sintered unexpanded tube sections, spaced apart from the first access porthole formed therein. A second hole is provided in the port collar overlying and in fluid communication with the second access porthole. The flexible access tube is preferably formed as a dual lumen tube, the first lumen being in fluid communication with the first hole in the port collar, and the second lumen being in fluid communication with the second hole in the port collar. The slide member of the valve structure establishes or interrupts fluid communication between the first access porthole and the first lumen, and simultaneously establishes or interrupts fluid communication between the second access porthole and the second lumen, as the slide member is moved between its opened and closed positions, respectively. First and second connectors are provided at the second end of the flexible access tube to couple the first and second lumens, respectively, to dialysis equipment.

The access fistula generally described above is surgically implanted through an incision in the skin, and the free ends of the expanded PTFE tube sections are joined to an artery and to a vein to establish a flow of blood through the PTFE tubing. The slide valve member is left in its opened position, and the incision is then closed with only the flexible access tubing extending therefrom. As explained above, box access is obtained through the second end of the flexible access tube while the access fistula heals. A second incision is later made above the port collar to permit a physician to move the valve slide member to its closed position; the flexible access tube is then cut off from the port collar, and the second incision is then closed, leaving the access fistula entirely below the skin for percutaneous cannulation thereafter.

DETAILED DESCRIPTION OF THE PREFERRED EMBODIMENTS

Figure 1:
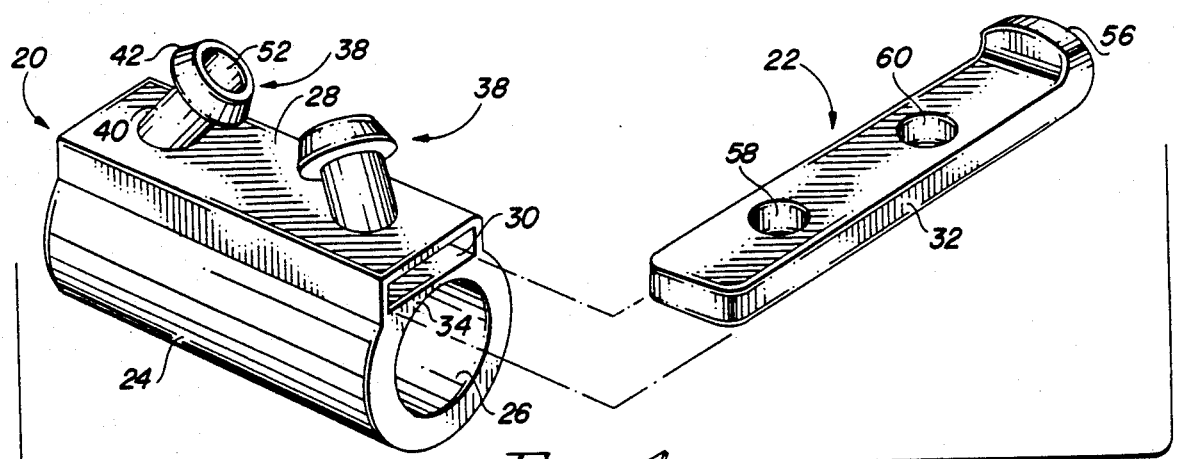
FIG. 1 is a perspective, exploded view of a port collar and cooperating slide valve member used in constructing an access fistula according to one preferred embodiment of the present invention.

Referring to FIG. 1, a port collar and associated slide valve member are shown for use in constructing one preferred embodiment of the present invention. The port collar is designated generally by reference numeral 20, while the associated slide valve member is designated by reference numeral 22. Port collar 20 has a generally cylindrical body 24 in which a first longitudinal circular bore 26 is formed. The upper portion of cylindrical body 24 is formed as an elongated, rectangular shape having an upper surface 28. A second longitudinal bore 30 is formed within the upper rectangular portion of port collar 20 and extending generally parallel to circular bore 26. As shown in FIG. 1, bore 30 may be rectangular in cross section. The internal cross-sectional dimensions of bore 30 are formed to be commensurate with the external cross-sectional dimensions of the elongated portion 32 of slide valve member 22. As will be noted in FIG. 2A, rectangular bore 30 is spaced apart from circular bore 26 by dividing wall 34.

Figure 2A:
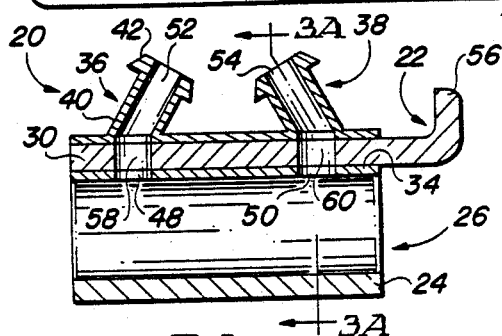
FIGS. 2A and 2B are cross-sectional views of the port collar shown in FIG. 1, and illustrating opened and closed positions of the slide valve member, respectively.
Figure 4:
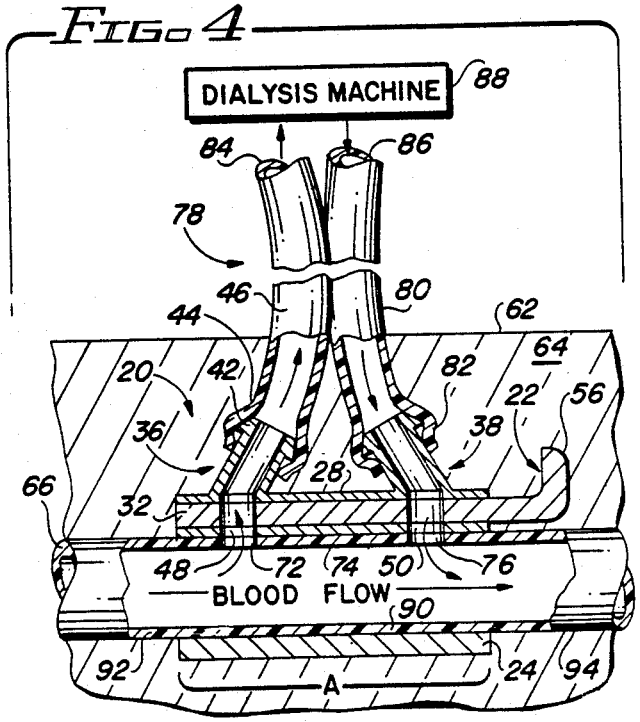
FIG. 4 is a cross-sectional view of an access fistula formed by combining the port collar of FIG. 1 with a specially constructed PTFE tube and a dual lumen flexible access tube.

Extending upwardly from upper surface 28 of port collar 20 are first and second tubular connectors 36 and 38 molded integrally with port collar 20. As shown in FIGS. 1 and 2A, tubular connector 36 includes a neck portion 40 terminating at its upper end in a barbed flange 42. Referring briefly to FIG. 4, tubular connector 36 is adapted to be received within and retain a first end 44 of a flexible tube 46 to be described in greater detail below.

Figure 2B:
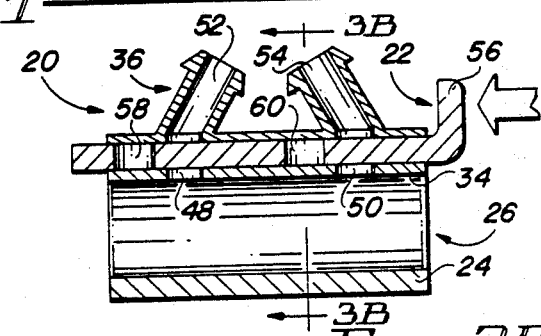

Referring to FIGS. 2A and 2B, a first hole 48 extends through separating wall 34 of port collar 20. A second hole 50, spaced apart longitudinally from first hole 48, also extends through separating wall 34 of port collar 20. Hole 48 continues upwardly through upper surface 28 of port collar 20 and communicates with a central bore 52 extending within tubular connector 36. Similarly, hole 50 extends upwardly through upper surface 28 of port collar 20 and communicates with a central bore 54 formed within tubular connector 38.

As shown in FIG. 1, the elongated portion 32 of slide valve member 22 is of a length commensurate with or slightly longer than port collar 20. Slide valve member 22 includes an upturned tab portion 56 which serves as a handle to operate slide valve member 22. Formed within elongated portion 32 of slide valve member 22 are a first hole 58 and a second hole 60 spaced apart longitudinally from each other by the same distance by which holes 48 and 50 of port collar 20 are separated.

As shown in FIGS. 2A and 2B, slide valve member 22 is adapted to be slidingly inserted within rectangular bore 30 of port collar 20. FIG. 2A illustrates the opened position of slide valve member 22 wherein hole 58 is overlying and aligned with hole 48 of port collar 20, and wherein hole 60 is overlying and aligned with hole 50 of port collar 20. In this opened position, an unobstructed fluid communication path is established between hole 48 and bore 52 of tubular connector 36. Similarly, an unobstructed fluid communication path is simultaneously established between hole 50 and bore 54 in tubular connector 38.

Figure 3A:
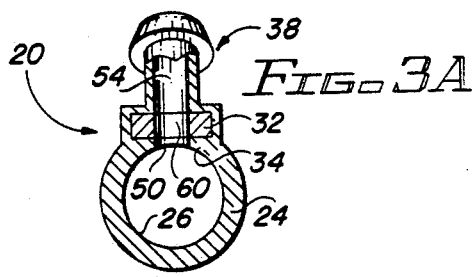
FIGS. 3A and 3B are cross-sectional views taken through lines 3A—3A and through lines 3B—3B, as shown in FIGS. 2A and 2B, respectively.
Figure 3B:
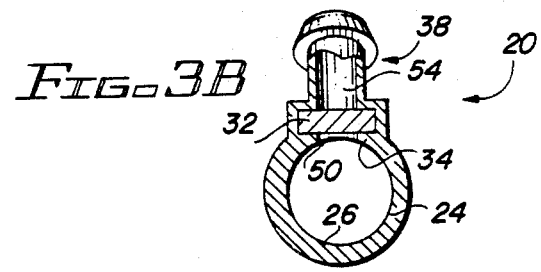

Referring now to FIGS. 2B and 3B, slide valve member 22 is shown after being fully advanced into rectangular bore 30 to assume its closed position. When slide valve member 22 is in its closed position, passageways 58 and 60 are simultaneously positioned out of alignment with holes 48 and 50, respectively, of port collar 20. Accordingly, holes 48 and 50 are simultaneously sealed off from bores 52 and 54 within tubular connectors 36 and 38, respectively. Thus, advancing slide valve member 22 to its closed position simultaneously interrupts the fluid communication paths established when slide valve member 22 is in the aforementioned opened position.

Both port collar 20 and slide valve member 22 are made of solid plastic, such as soft polyurethane. Any durometer implantable plastic material may be used to form port collar 20 and slide valve member 22. These components may be either machined or molded to form the structures described above.

FIG. 4 illustrates a blood access device according to one preferred embodiment of the present invention using port collar 20 and slide valve member 22 as described above in regard to FIGS. 1-3. FIG. 4 illustrates the access device, or access fistula, immediately following initial implantation within the vascular system of a living body. In FIG. 4, reference numeral 62 designates the outer layer of skin, while the tissues lying therebelow are designated by reference numeral 64. As shown in FIG. 4, port collar 20 extends over and around a prosthetic vascular graft formed by tube 66. The outer diameter of tube 66 is commensurate with the inner diameter of circular bore 26 of port collar 20. Preferably, port collar 20 is secured to tube 66 by a press fit. To insure that the port collar stays properly positioned, port collar 20 may be designed so that cylindrical bore 26 has an inner diameter slightly less than the outer diameter of the central portion of tube 66; port collar 20 is then forced over the central portion of tube 66 under slight pressure until port collar 20 and tube 66 are properly positioned relative to one another.

Figure 6:
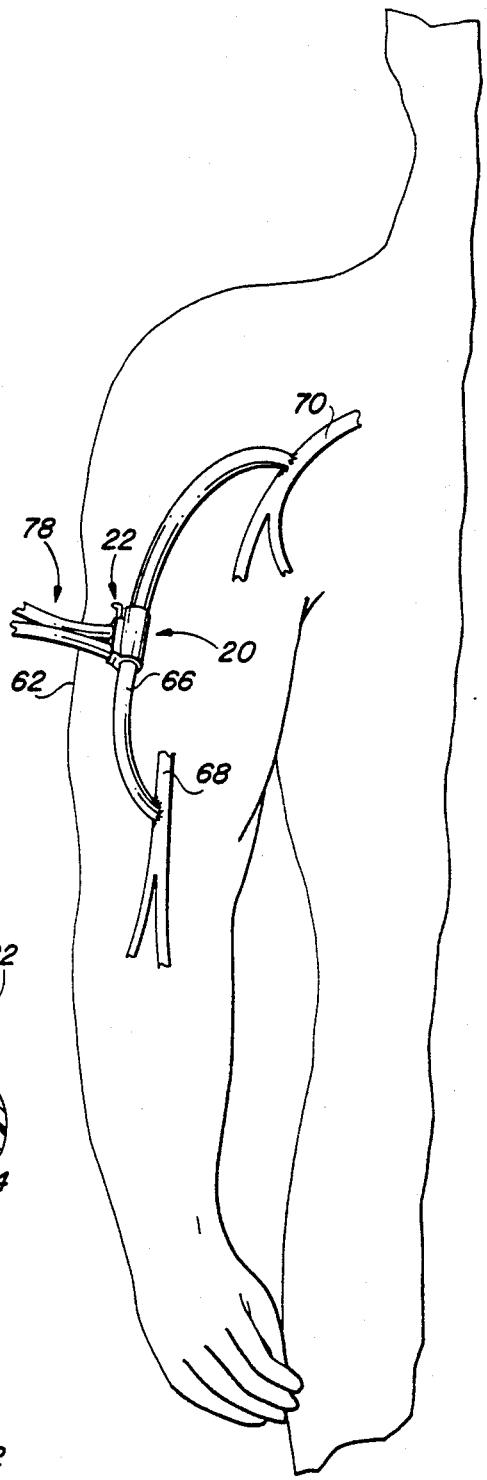
FIG. 6 illustrates the manner in which an access fistula of the type described herein would be implanted between an artery and a vein in the upper arm.

Referring briefly to FIG. 6, the opposing ends of tube 66 forming the prosthetic vascular graft are joined to an artery 68 and a vein 70, respectively, by performing arterial anastomosis and venous anastomosis in an end-to-side fasion, in order to induce a flow of blood through tube 66.

Referring again to FIG. 4, a first access port hole 72 is formed within the tubular wall 74 of tube 66 for permitting access to the interior of tube 66 through tubular wall 74. Access port hole 72 is aligned with hole 48 in port collar 20. Similarly, a second access port hole 76 is formed in tubular wall 74 of tube 66 and aligned with hole 50 in port collar 20. Thus, holes 48 and 50 in port collar 20 are in full communication with access port holes 72 and 76, respectively.

Also shown in FIG. 4 is a dual lumen flexible access tube designated generally by reference numeral 78. Dual lumen access tube 78 includes a first lowermost end which branches off into a first flexible access tube 46 and a second flexible access tube 80. As mentioned above, tube 46 has a lowermost end 44 engaged over and around barbed flange 42 of tubular connector 36. Similarly, the lowermost end 82 is engaged over and around a similar barbed flange provided on tubular connector 38. Tube 46 defines a first lumen which extends from lowermost end 44 of tube 46 to opposing second end 84. Similarly, access tube 80 defines a second lumen extending from lowermost end 82 to opposing upper end 86. Ends 84 and 86 of access tubes 46 and 80, respectively, may be provided with conventional luer connectors (not shown) to facilitate interconnection of dual lumen tubing 78 to a dialysis machine 88 to remove wastes from the blood flow system. Conventional tubing clamps (not shown) may be provided proximate distal ends 84 and 86 of tubes 46 and 80 for discontinuing blood flow through the flexible access tubes after a dialysis session has been completed. The aforementioned luer connectors may then be capped until the next dialysis session. Such dual lumen access tubing 78 can be made from almost any type of soft plastic, with polyurethane, silastic or polyvinyl chloride (PVC) being the most preferred materials.

Still referring to FIG. 4, with slide valve member 22 in the opened position, blood flowing within tube 66 passes upwardly through access port hole 72 and hole 48, through passageway 58 of slide valve member 22, and through bore 52 of tubular connector 36, for passage to dialysis machine 88 via access tube 46. Purified blood is then conveyed by access tube 80 through bore 54 of tubular connector 38, through passageway 60 of slide valve member 22, and through hole 50 and access port hole 76 back into tube 66 for return to the blood flow system. Tubular connectors 36 and 38 are inclined at an angle of approximately 30° from a plane perpendicular to tube 66 to minimize admixing and recirculation of purified blood returned by access port hole 76 with the blood flowing into access port hole 72.

Figure 5:
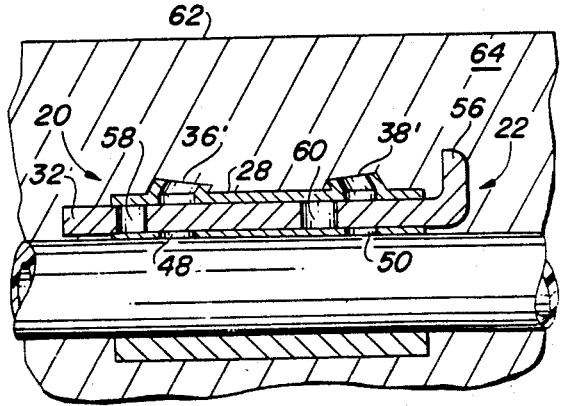
FIG. 5 is a cross-sectional view of the access fistula shown in FIG. 4 after the slide valve member thereof has been closed and the dual lumen flexible access tube has been cut off from the port collar.

After the prosthetic vascular graft tube 66 has been allowed sufficient time to heal, the flexible dual lumen access tubing 78 is no longer needed to obtain access to the vascular system. Accordingly, an incision is then made in the skin 62 proximate port collar 20 for allowing the physician access to slide valve member 22. As shown in FIG. 5, the physician advances slide valve member 22 into port collar 20 to seal off holes 48 and 50 from tubular connectors 36 and 38. The physician then inserts a scalpel through the aforementioned incision and cuts through tubular connectors 36 and 38 proximate upper surface 28 of port collar 20, such that tubular connectors 36 and 38 then terminate at the points designated 36' and 38', respectively. The incision is then closed. Access to the vascular system may then be made in the conventional manner by percutaneous cannulation of prosthetic vascular graft tube 66 in an area remote from port collar 20. As shown in FIG. 5, after tubular connectors 36 and 38 are severed, dual lumen access tubing 78 is removed, and the access fistula, including port collar 20, lies entirely below outer skin 62.

Referring again to FIG. 4, the region of tube 66 surrounded by port collar 20 is designated by A. This region of tube 66 must be sufficiently rigid to permit port collar 20 to be press fit or otherwise sealingly secured thereto. While expanded PTFE tubing is a preferred material for forming prosthetic vascular grafts, such expanded PTFE tubing is not sufficiently rigid to allow a port collar to be easily secured thereto. Moreover, it is difficult to form well defined access port holes within such expanded PTFE tubing. Accordingly, it might be possible to form prosthetic vascular graft tube 66 as a relatively rigid tube section 90 made of a material other than PTFE, and attaching to the opposing ends thereof opposing pliable sections 92 and 94 of expanded PTFE tubing to facilitate implantation within the vascular system and to further facilitate percutaneous cannulation. However, the use of a discrete, rigid tube section 90 that is not integral and continuous with surrounding pliable tube sections 92 and 94 would give rise to discontinuities at those points where rigid tube section 90 is joined with pliable tube sections 92 and 94. Such discontinuities may provide sites for clotting and thrombosis to occur.

Accordingly, in the preferred embodiment of the present invention, prosthetic vascular graft tube 66 is formed on a single, continuous length of PTFE tubing which provides a smooth, continuous blood flow lumen, thereby minimizing blood clotting and thrombosis. The portion A of the PTFE tubing to ultimately lie within port collar 20 is maintained relatively rigid, while the opposing, surrounding portions 92 and 94 are maintained soft, porous and pliable as in conventional PTFE vascular grafts. The rigid portion 90 of the PTFE tubing is sufficiently rigid that blood access port holes 72 and 76 may easily be tapped into the tubular sidewall thereof. The manner in which such a PTFE tube may be fabricated will now be described below.

Tube section 90 of PTFE tube 66 consists of a hard, sintered unexpanded length of PTFE. Pliable PTFE tube section 92 has a first end integrally joined with tube section 90 and a second end adapted to be joined to an artery or vein within the living body. Similarly, pliable tube section 94 has a first end adapted to be interconnected with an artery or vein within the vascular system, and a second end integrally joined with a second end of hard, sintered unexpanded PTFE tube section 90. Two different methods may be used to selectively spot sinter a portion of an expanded PTFE tube to cause the selected portion to remain unexpanded. Both methods provide a tube with a smooth continuous lumen in which an unexpanded, or hard, section is adjacent and integral with uniformly expanded sections.

In the first method, known as pre-sintering, the steps normally used to manufacture expanded PTFE tubing are followed, up until the step of removing the lubricant from the extrudate. Such conventional steps include the addition of lubricant to a PTFE resin, preforming the mixture into a billet by applying pressure thereto, extruding the preformed billet into a tube of selected dimension, and then evaporating out the aforementioned lubricant. The resulting extruded PTFE tubes, commonly referred to as dried extrudate, are then wrapped with a heat reflecting material, such as tin foil, exposing only those areas which are to remain rigid and unexpanded. The selectively exposed tube is then rotated over a source of heat which is at or near the sintering temperature of PTFE (approximately 327°–341° C.). The exposed portion of the PTFE tube changes in appearance from being white in color to being virtually clear when sintering has been accomplished. The tube is then removed from the heat source and cooled to a temperature below the aforementioned sintering temperature. After cooling, the fabrication process is completed by expanding the tube at a temperature below the aforementioned sintering temperature, and then sintering the newly expanded tube. The resulting structure is an expanded PTFE tube having hard, sintered portions that are unexpanded in those regions where the tube was exposed to sintering temperatures prior to being expanded.

A second method, known as post-sintering, may also be used to provide a PTFE tube having hard, sintered, unexpanded portions adjacent to uniformly expanded sections. In this second method, the PTFE tube is fully expanded using conventional processing for expanded PTFE tube products. The uniformly expanded and sintered PTFE tube is then mounted on a stainless steel mandrel having an outside diameter which matches the inside diameter of the expanded tube. The tube is then compressed by applying pressure at both ends of the tube and returned to approximately its prior, unexpanded length. The tube is then secured at such compressed length upon the mandrel and wrapped with a heat reflecting material, exposing only those portions which are to remain hard. The selectively shielded tube is then rotated over a source of heat which is at or near the aforementioned sintering temperature of PTFE. After sintering is complete, the tube is removed from the mandrel and allowed to stretch back to its originally expanded length, but including hard sintered, unexpanded areas in those regions which were exposed to the aformentioned heat source.

Both the pre-sintering method and post-sintering method described above allow the formation of any number of hard sintered unexpanded sections along an expanded PTFE tube. These hard sections can be used for physical connections, formation of well defined ports, or other purposes that are not readily achieved with relatively soft expanded PTFE tubing. Such hard sintered, unexpanded regions may be formed within a continuous length of expanded PTFE tubing without creating a significant discontinuities, thereby maintaining a smooth continuous lumen.

Referring to FIG. 4, formation of the access fistula tube 66 through the use of a PTFE tube having a hard sintered, unexpanded section 90 surrounded by expanded PTFE sections 92 and 94 facilitates both securing port collar 20 to PTFE tube 66, as well as the formation of well defined access port holes 72 and 76. PTFE tube 66 provides a smooth, continuous flow surface, while the access port holes and communicating port collar can accommodate flow rates up to 400 ml. per minute, with little or no recirculation of the blood flowing into and out of the access fistula. The described access fistula provides for both acute and chronic vascular access, and thereby eliminates either the need for a catheter placement procedure or the need to prematurely puncture a vascular graft before it has become well healed.

During manufacture of the access fistula shown in FIG. 4, it is necessary to properly align port collar 20 and access port holes 72 and 76 formed within PTFE tube 66. The port collar holes 48 and 50 are created during the plastic molding of port collar 20 itself, and accordingly, holes 48 and 50 remain at a constant orientation. The access portholes may be formed in the tubular wall of the hard sintered, unexpanded portion of PTFE tube 66 by securing tube section 90 in a jig and drilling the access port holes at the desired sites. Port collar 20 is then slid over expanded portion 94 of the access fistula until it reaches unexpanded portion 90. Port collar 20 is then rotated until holes 48 and 50 align with access port holes 72 and 76, respectively. This alignment may be checked by attempting to introduce tightly fit pins through bores 52 and 54 of tubular connectors 36 and 38 and down into the central lumen of tube 66, while slide valve member 22 is in its opened position. Port collar 20 may be manipulated until the aforementioned alignment pins easily slide through both sets of corresponding holes.

Another method to align access port holes 72 and 76 with holes 48 and 50 of port collar 20 is to position port collar 20 over hard sintered, unexpanded PTFE tube section 90 prior to drilling the access port holes. A drill bit can then be introduced through each of tubular connectors 36 and 38 to form access port holes 72 and 76 through the tubular wall of PTFE tube 66. Proper alignment may then be verified by attempting to slide alignment pins down into the lumen of PTFE tube 66 in the manner described above. Such alignment pins may also be used to verify the slide valve member 22 has initially been positioned in its opened position prior to packaging and shipment.

The above-described access fistula may be implanted using current techniques for implanting conventional bridge arteriovenous fistulas, employing either a loop or straight configuration. The flexible access tubing initially secured to the access fistula protrudes through the skin at normally existing incisions, so no additional incisions are required during implantation.

The patient may be dialyzed immediately after surgery in the same manner as is presently used with catheters or other types of access shunts. This method of dialysis is used for approximately the next two week period to allow the expanded PTFE portions of the access fistula to heal and receive tissue ingrowth. After approximately two weeks the patient returns to the surgeon's office to have the access portion of the fistula taken down under local anesthesia.

After local anesthesia is administered, the surgeon makes a small incision above the port collar and exposes the slide valve member 22 and tubular connectors 36 and 38. This small additional incision need only extend one or two centimeters adjacent the original surgical incision through which flexible access dual lumen tubing 78 extends. The slide valve member is then moved to its closed position (see FIG. 5) using any surgical instrument, or the surgeon's fingers. Next, dual lumen tubing 78 is severed just above the skin 62, and the remainder of the flexible access tubing is discarded. The surgeon then carefully severs from port collar 20 both tubular connectors 36 and 38, and pulls these connectors, along with the remaining portions of dual lumen 78, through the newly formed incision. Closing is then accomplished by suturing closed the now vacant dual lumen tubing exit site, as well as the supplemental incision. The fistula is then used as a normal expanded PTFE arteriovenous fistula which may be cannulated with needles whenever dialysis is necessary. The position of the implanted port collar 20 below the skin may easily be determined by palpation and avoided during cannulation.

Figure 7:
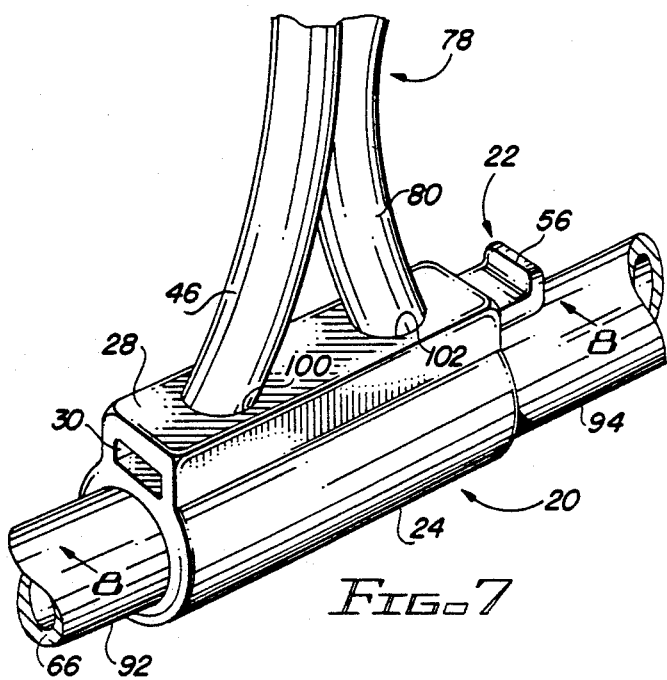
FIG. 7 is a perspective view of an alternate embodiment of the present invention wherein the end of the dual lumen access tube coupled to the port collar is molded therein.
Figure 8:
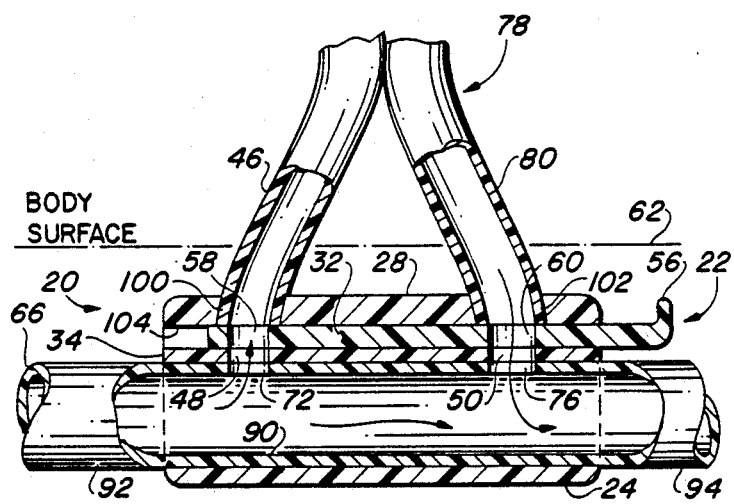
FIG. 8 is a cross-sectional view of the access fistula shown in FIG. 7 wherein the slide valve member is shown in its opened position for acute access to the blood flow system.
Figure 9:
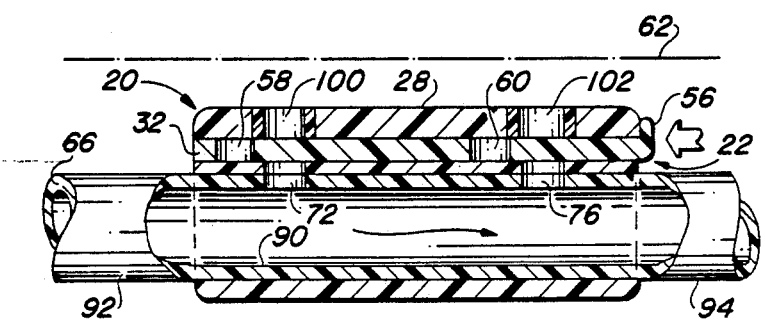
FIG. 9 is a further cross-sectional view of the access fistula shown in FIG. 7 following closure of the slide valve member, and following the surgical removal of the flexible access tubing from the port collar.

FIGS. 7, 8 and 9 show an alternate embodiment of the present invention. Those features which are in common with those shown in FIG. 4 are labelled by corresponding reference numerals. Tubular connectors 36 and 38 shown in FIGS. 1-4 are eliminated in the alternate embodiment shown in FIGS. 7-9. Instead, plastic port collar 20 is molded around the lowermost end 100 of access tube 46 and molded around lowermost end 102 of access tube 80. As mentioned above, port collar 20 is preferably formed from a solid plastic material, such as soft polyurethane. Such plastic materials are easily molded, and the plastic mold (not shown) from which port collar 20 is molded includes apertures of a size commensurate with the outer diameter of access tubes 46 and 80, allowing the lowermost ends 100 and 102 thereof, respectively, to be inserted into the mold prior to filling the mold with plastic. Lowermost ends 100 and 102 of access tubes 46 and 80, respectively, are inserted into the mold to a depth corresponding to the upper wall 104 of rectangular bore 30 in order to avoid interference with the passage of slide valve member 22. By molding the plastic material forming port collar 20 about the lowermost ends 100 and 102 of access tubes 46 and 80, a substantially leak proof seal is formed between upper surface 28 of port collar 20 and the lowermost ends of flexible access tube 78. Slide valve member 22 operates in the same manner as described above in regard to the embodiment of the invention shown in FIGS. 1-4.

The access fistula shown in FIG. 8 is implanted within a patient in the same manner as described above with regard to FIG. 6. While the access fistula heals following implantation, acute access to the blood flow system is obtained through flexible access tube 78 in the manner explained above. After body tissue grows into the expanded PTFE tube portions of fistula tube 66, the physician makes an incision above port collar 20 and moves slide valve member 22 to the closed position, as shown in FIG. 9, thereby sealing access port holes 72 and 76 from lowermost ends 100 and 102 of access tubes 46 and 80, respectively. Using a scalpel, the physician then cuts access tubes 46 and 80 as close to being flush as possible with upper surface 28 of port collar 20, leaving lowermost ends 100 and 102 of access tubes 46 and 80 embedded within the upper portion of port collar 20. The remainder of the access tubing is discarded, and the incisions are closed in the manner described above.

Those skilled in the art will now appreciate that an improved access fistula has been described which provides for both acute and chronic vascular access, eliminating the need for any catheter placement procedure, and further avoiding permanent passage through the skin to lessen the risk of infection. The improved access fistula provides a smooth, continuous flow surface, thereby lessening the risk of thrombosis. Moreover, the risks of hematoma formation associated with premature graft punctures is avoided, thereby extending the life expectancy of the fistula, without significantly complicating conventional implantation surgical procedures. While the present invention has been described with reference to preferred embodiments thereof, the description is for illustrative purposes only and is not to be construed as limiting the scope of the invention. Various modifications and changes may be made by those skilled in the art without departing from the true spirit and scope of the invention as defined by the appended claims.

We claim:

1. An access device for implantation in a living body to facilitate access to a fluid path within the living body, said access device comprising in combination:
   a. a hard sintered unexpanded PTFE tube section having first and second opposing ends and having a tubular wall;
   b. at least one access port hole formed in the tubular wall of said hard sintered unexpanded PTFE tube section for permitting access to the interior thereof;
   c. first and second expanded PTFE tube sections each having first and second opposing ends, the first end of said first expanded PTFE tube section being integrally joined with the first end of said hard sintered unexpanded PTFE tube section, and the first end of said second expanded PTFE tube section being integrally joined with the second end of said hard sintered unexpanded PTFE tube section;
   d. said first and second expanded PTFE tube sections and said hard sintered unexpanded PTFE tube section collectively providing a PTFE tube having a smooth continuous lumen; and
   e. access means coupled to said hard sintered unexpanded PTFE tube section for establishing a fluid path between the at least one access port hole and a point external to the living body.

2. An access device for implantation within a fluid path of a living body, said access device being intended to be implanted at least partially below an outer skin of the living body, said access device comprising in combination:
   a. a PTFE tube including:
      i. a hard sintered unexpanded PTFE tube section having first and second opposing ends and having a tubular wall;
      ii. at least one access port hole formed in the tubular wall of said hard sintered unexpanded PTFE tube section for permitting access to the interior of said PTFE tube through the tubular wall of said hard sintered unexpanded PTFE tube section; and
      iii. first and second unexpanded PTFE tube sections each having first and second opposing ends, the first end of said first unexpanded PTFE tube section being integral with the first end of said hard sintered unexpanded PTFE tube section, and the first end of said second expanded PTFE tube section being integral with the second end of said hard sintered unexpanded PTFE tube section;

iv. said first and second expanded PTFE tube sections and said hard sintered unexpanded PTFE tube section collectively providing a PTFE tube having a smooth continuous lumen; and b. a port collar secured to said hard sintered unexpanded PTFE tube section, said port collar having at least one hole formed therein in fluid communication with said at least one access port hole formed in the tubular wall of said hard sintered unexpanded PTFE tube section for permitting fluid access to said smooth continuous lumen.

3. An access device as recited by claim 2 wherein said port collar extends around the tubular wall of said hard sintered unexpanded PTFE tube section, said port collar having a central bore receiving said hard sintered unexpanded PTFE tube section and being sealingly engaged therewith.

4. An access device as recited by claim 3 wherein said port collar is formed from a durometer implantable plastic material.

5. An access device as recited by claim 4 wherein said port collar is formed of a soft polyurethane.

6. An access device as recited by claim 2 further including a flexible tube having at least one lumen, said flexible tube having first and second opposing ends, the first end of said flexible tube being coupled to said port collar for coupling said at least one lumen of said flexible tube to said at least one hole formed in said port collar in order to establish fluid communication between said at least one lumen of said flexible tube and said PTFE tube, said flexible tube being adapted to extend through the skin of the living body to facilitate access to said fluid path of the living body via the second end of said flexible tube.

7. An access device as recited by claim 6 wherein said flexible tube is formed of soft plastic.

8. An access device as recited by claim 6 wherein:
a. said hard sintered unexpanded PTFE tube section has a second access port hole formed in the tubular wall thereof for permitting access to the interior of said PTFE tube, said second access port hole being spaced apart from said at least one access port hole;
b. said port collar having a second hole formed therein in fluid communication with said second access port hole for permitting fluid access to said smooth continuous lumen; and
c. said flexible tube including a second lumen, the first end of said flexible tube coupling the second lumen to said second hole formed in said port collar in order to establish fluid communication between the second lumen of said flexible tube and said PTFE tube.

9. An access device as recited by claim 8 wherein the second end of said flexible tube includes first and second connectors coupled with said at least one lumen and said second lumen, respectively, for establishing independent fluid connections thereto.

10. An access device as recited by claim 8 wherein said port collar includes valve means for selectively interrupting fluid communication between said at least one lumen of said flexible tube and said at least one access port hole, and simultaneously interrupting fluid communication between said second lumen of said flexible tube and said second access port hole.

11. An access device as recited by claim 6 wherein said port collar includes valve means for selectively interruping fluid communication between said at least one lumen of said flexible tube and said at least one access port hole formed in the tubular wall of said hard sintered unexpanded PTFE tube section 12. An access device as recited by claim 11 wherein said port collar is adapted to be implanted entirely below the skin.

13. An access device as recited by claim 11 wherein said port collar includes a tubular connector extending therefrom to receive the first end of said flexible tube, said tubular connector being in fluid communication with said at least one hole formed in said port collar, said tubular connector being adapted to be cut off from said port collar below the skin after said valve means is closed to interrupt fluid communication between said at least one lumen of said flexible tube and said at least one access port hole.

14. An access device as recited by claim 11 wherein said port collar is formed of an implantable plastic material, and wherein said port collar is molded around the first end of said flexible tube to establish fluid communication between said at least one lumen of said flexible tube and said at least one hole formed in said port collar, said first end of said flexible tube being adapted to be cut off from said port collar substantially flush therewith after said valve means is closed.

15. An access device as recited by claim 13 wherein said port collar is adapted to be implanted entirely below the skin.

16. An access device for implantation within a fluid path of a living body, said access device being intended to be implanted at least partially below an outer skin of the living body, said access device comprising in combination:

a. a PTFE tube having predetermined outer diameter and including:
  i. a hard sintered unexpanded PTFE tube section having first and second opposing ends and having a tubular wall;
  ii. first and second access port holes formed in the tubular wall of said hard sintered unexpanded PTFE tube section for permitting access to the interior of said PTFE tube through the tubular wall of said hard sintered unexpanded PTFE tube section;
  iii. first and second unexpanded PTFE tube sections each having first and second opposing ends, the first end of said first unexpanded PTFE tube section being integral with the first end of said hard sintered unexpanded PTFE tube section, and the first end of said second expanded PTFE tube section being integral with the second end of said hard sintered unexpanded PTFE tube section;
  iv. said first and second expanded PTFE tube sections and said hard sintered unexpanded PTFE tube section collectively providing a PTFE tube having a smooth continous lumen; and b. a port collar having a generally cylindrical shape and having a first longitudinal circular bore of a diameter commensurate with the predetermined outer diameter of said PTFE tube, said port collar being secured to said PTFE tube with said hard sintered PTFE tube section being disposed substantially within said first longitudinal circular bore, said port collar having first and second holes formed therein in fluid communication with said first and second access port holes, respectively; and.

c. flexible tube means having first and second ends and having first and second lumens extending between said first and second ends thereof, the first end of said flexible tube means being coupled to said port collar for establishing fluid communication between the first lumen and the first access port hole and between the second lumen and the second access port hole, the flexible tube means being adapted to extend through the skin of the living body to facilitate access to the fluid path of the living body via the second end of said flexible tube means.

17. An access device as recited by claim 16 wherein the second end of said flexible tube means includes first and second connectors coupled with said first and second lumens, respectively, for establishing independent fluid connections thereto.

18. An access device as recited by claim 16 wherein said port collar includes valve means for selectively interrupting fluid communication between said first lumen and said first access port hole, and simultaneously interrupting fluid communication between second lumen and said second access port hole.

19. An access device as recited by claim 18 wherein said port collar has a second longitudinal bore formed therein parallel to said first longitudinal bore, said second longitudinal bore having predetermined cross-sectional dimensions; the first and second holes formed in said port collar communicating with said second longitudinal bore, and said valve means including an elongated member having cross-sectional dimensions commensurate with said predetermined cross-sectional dimensions of said second longitudinal bore for permitting said elongated member to slide within said second longitudinal bore, said elongated member having first and second transverse passageways formed therein, said elongated member adapted to assume a first opened positioned wherein said first and second passageways are in alignment with the first and second holes in said port collar to provide fluid communication between said first and second lumens and the first and second access port holes, respectively, and being adapted to assume a second closed position wherein said first and second passageways are out of alignment with the first and second holes in said port collar to seal said first and second lumens from said first and second access port holes, respectively.

20. An access device as recited by claim 18 wherein said flexible tube means is adapted to be cut off from said port collar below the skin, proximate to the first end of said flexible tube means, after said valve means is moved to its closed position to interrupt fluid communication between said first and second lumens and said first and second access port holes, respectively.

21. A method of providing access to the blood flow system of a living body, said method comprising the steps of:

a. creating a first incision through the skin of the living body;
b. implanting through such first incision an access fistula including:
 i. an implantable graft having a relatively rigid tube section surrounded by and continuous with first and second opposing pliable tube sections, the relatively rigid tube section having at least one access port hole formed in the tubular wall thereof;
 ii. a flexible access tube having a first end disposed proximate to the relatively rigid tube section of the implantable graft and having an opposing second end; and
 iii. a valve disposed between the relatively rigid tube section of the implantable graft and the first end of the flexible access tube, the valve having an opened position for selectively providing fluid communication between the flexible access tube and the at least one access port hole, and having a closed position for selectively sealing the flexible access tube from the at least one access port hole;
c. joining the first and second opposing pliable tube sections of the implantable graft with an artery and a vein, respectively, of the blood flow system of the living body to establish a flow of blood through the implantable graft;
d. insuring that the valve is initially in its opened position;
e. closing the first incision over the access fistula while permitting the flexible access tube to extend outwardly through the first incision with the second end of the flexible access tube external from the living body;
f. temporarily accessing the blood flow system of the living body via the second end of the flexible access tube to permit ingrowth of body tissues into the implantable graft;
g. creating a second incision proximate the valve of the implantable graft to permit access to the valve after awaiting the ingrowth of body tissues into the implantable graft;
h. moving the valve to its closed position;
i. cutting off the flexible access tube from the implantable graft, and removing the flexible access tube from the living body;
j. closing the second incision leaving the implantable graft and valve implanted below the skin; and
k. thereafter accessing the blood flow system via the percutaneous cannulation of the implantable graft.

22. A method as recited by claim 21 wherein the implantable graft is made from PTFE, the relatively rigid tube section being hard sintered unexpanded PTFE, and the first and second pliable tube sections being expanded PTFE integrally joined with the hard sintered unexpanded PTFE tube section.

* * * * *